(12) United States Patent
Dudley et al.

(10) Patent No.: US 9,308,334 B2
(45) Date of Patent: Apr. 12, 2016

(54) INHALER

(75) Inventors: Steven Dudley, Brighton (GB); John Palmer-Felgate, West Sussex (GB); Sean Reynolds, West Sussex (GB); Iain Breakwell, West Sussex (GB); Jon Jamin, Suffolk (GB); Steve Augustyn, Bucks (GB); Grant Smetham, Surrey (GB); Laura Kaye, Cambridge (GB); John McGarva, St. Neots (GB)

(73) Assignee: Novartis AG, Basel (CH)

( * ) Notice: Subject to any disclaimer, the term of this patent is extended or adjusted under 35 U.S.C. 154(b) by 314 days.

(21) Appl. No.: 13/876,601

(22) PCT Filed: Sep. 28, 2011

(86) PCT No.: PCT/EP2011/066941
§ 371 (c)(1),
(2), (4) Date: Mar. 28, 2013

(87) PCT Pub. No.: WO2012/041938
PCT Pub. Date: Apr. 5, 2012

(65) Prior Publication Data
US 2013/0206142 A1      Aug. 15, 2013

Related U.S. Application Data

(60) Provisional application No. 61/388,317, filed on Sep. 30, 2010, provisional application No. 61/485,922, filed on May 13, 2011.

(51) Int. Cl.
*A61M 15/00* (2006.01)
*A61M 16/16* (2006.01)
(Continued)

(52) U.S. Cl.
CPC ......... *A61M 15/0045* (2013.01); *A61M 15/001* (2014.02); *A61M 15/0026* (2014.02);
(Continued)

(58) Field of Classification Search
CPC ............... A61M 15/0003; A61M 15/0045; A61M 2205/12; A61M 2205/121; A61M 2205/123
USPC .......................... 128/203.12, 203.15, 203.21
See application file for complete search history.

(56) References Cited

U.S. PATENT DOCUMENTS 4,653,494 A * 3/1987 Ruderian .............. A61M 15/00
128/203.22
(Continued)

FOREIGN PATENT DOCUMENTS

EP      2082758 A1      7/2009
EP      2082761 A1      7/2009
(Continued)

OTHER PUBLICATIONS

International Search Report, PCT/EP2011/066941 (Apr. 2, 2012).

*Primary Examiner* — Tan-Uyen (Jackie) T Ho
*Assistant Examiner* — Joseph D Boecker
(74) *Attorney, Agent, or Firm* — Michael Mazza

(57) ABSTRACT

An inhaler, the inhaler including a body (104) and a cartridge (106), the cartridge comprising a dose storage portion (122) and an airway (124), the dose storage portion being suitable for containing a plurality of doses of an inhalable medicament, the airway including a mouthpiece (128) at an end thereof, the inhaler device configured and arranged such that a dose of inhalable medicament from the dose storage portion can be accessed and arranged in a delivery configuration for delivery to a user through the airway upon inhalation through the mouthpiece by the user, the inhaler characterized in that the cartridge is replaceably removable from the body.

9 Claims, 4 Drawing Sheets

(51) Int. Cl.
    *A61M 11/00* (2006.01)
    *A61M 16/00* (2006.01)

(52) U.S. Cl.
    CPC ....... *A61M15/0035* (2014.02); *A61M 15/0043* (2014.02); *A61M 15/0065* (2013.01); *A61M 15/0068* (2014.02); *A61M 15/0085* (2013.01); *A61M 16/161* (2014.02); *A61M 11/005* (2013.01); *A61M 2016/0015* (2013.01); *A61M 2016/0027* (2013.01); *A61M 2016/0033* (2013.01); *A61M 2202/064* (2013.01); *A61M 2205/273* (2013.01); *A61M 2205/276* (2013.01); *A61M 2205/3368* (2013.01); *A61M 2205/50* (2013.01); *A61M 2205/52* (2013.01); *A61M 2205/8206* (2013.01); *A61M 2230/50* (2013.01)

(56) References Cited

U.S. PATENT DOCUMENTS

| | | | | |
|---|---|---|---|---|
| 4,694,824 A * | 9/1987 | Ruderian | ............... | A61M 15/00 128/200.19 |
| 5,694,920 A | 12/1997 | Abrams et al. | | |
| 6,116,238 A * | 9/2000 | Jackson | ............ | A61M 15/0045 128/203.12 |
| 8,240,304 B2 * | 8/2012 | Thoemmes | ........... | A61M 15/00 128/200.14 |
| 8,763,606 B2 * | 7/2014 | Mosier | ............... | A61M 15/0045 128/203.12 |
| 2002/0011247 A1 * | 1/2002 | Ivri | ................... | A61M 15/0028 128/200.16 |
| 2004/0025877 A1 * | 2/2004 | Crowder | ........... | A61M 15/0045 128/203.15 |
| 2005/0154491 A1 * | 7/2005 | Anderson | ............. | A61M 15/00 700/236 |
| 2005/0172963 A1 | 8/2005 | Allan et al. | | |
| 2005/0177275 A1 | 8/2005 | Harvey et al. | | |
| 2005/0247306 A1 * | 11/2005 | Harvey | ................. | A61J 7/0481 128/200.21 |
| 2006/0157053 A1 * | 7/2006 | Barney | ............. | A61M 15/0045 128/200.23 |
| 2007/0215149 A1 * | 9/2007 | King | ................. | A61M 15/0028 128/203.12 |
| 2007/0221218 A1 * | 9/2007 | Warden | ............. | A61M 15/0045 128/203.15 |
| 2008/0001008 A1 * | 1/2008 | Thoemmes | ........... | A61M 15/00 239/338 |
| 2009/0194105 A1 | 8/2009 | Besseler et al. | | |
| 2010/0294278 A1 * | 11/2010 | Mosier | .............. | A61M 15/0045 128/203.14 |
| 2011/0036350 A1 | 2/2011 | Thoemmes | | |
| 2011/0277753 A1 * | 11/2011 | Dunne | ............. | A61M 15/0045 128/200.14 |
| 2015/0283338 A1 * | 10/2015 | Colosio | ............ | A61M 15/0028 128/203.15 |

FOREIGN PATENT DOCUMENTS

| | | |
|---|---|---|
| RU | 2379062 C2 | 3/2008 |
| WO | 0236188 A2 | 5/2002 |
| WO | 0236189 A1 | 5/2002 |
| WO | 2006071512 A1 | 7/2006 |
| WO | 2007121097 A2 | 10/2007 |
| WO | 2007137991 A1 | 12/2007 |

* cited by examiner

INHALER

BACKGROUND

The present invention relates to an inhaler, particularly to a multiple dose inhaler having a replaceable multi-dose storage portion.

Inhalers are devices that can be used to deliver a medicament to the lungs of a user inhaling through the device. When a user inhales through the device a mouthpiece is typically held in the mouth, or nose, of a user. If the device is used to deliver more than one dose, for example it is a single dose device and is charged with a capsule or blister for each use, or it is a multiple dose device which contains a replaceable dose store such as a blister disc having a plurality of doses thereon, it means that at least a portion of the device repeatedly contacts the user and, if not cleaned, may become contaminated. Many inhalers come with instructions defining a cleaning regime that a user should follow during the life span of the device to avoid such contamination causing a problem. However users do not always follow the instructions accurately.

Multiple dose inhalers are known which contain a plurality of individual doses, or a reservoir from which doses can be metered, and once all doses have been used the entire device is disposed of and a new device obtained. This naturally limits the time during which contamination can build up. However disposing of the entire device, particularly a complex device, when empty may have cost implications so refillable devices have been developed. For such refillable devices a component of the device must be replaced or refilled when required and the empty, or no longer useable, part will be disposed of.

SUMMARY OF THE INVENTION

The invention provides an inhaler, the inhaler including a body and a cartridge, the cartridge comprising a dose storage portion and an airway, the dose storage portion being suitable for containing a plurality of doses of an inhalable medicament, the airway including a mouthpiece at an end thereof, the inhaler device configured and arranged such that a dose of inhalable medicament from the dose storage portion can be accessed and arranged in a delivery configuration for delivery to a user through the airway upon inhalation through the mouthpiece by the user, the inhaler characterised in that the cartridge is replaceably attachable to the body.

By providing an inhaler with a replaceable cartridge which includes both a dose storage portion and an airway with a mouthpiece it is not possible for a user to forget to replace the mouthpiece and airway in accordance with a replacement cycle as it would be if a separate airway and mouthpiece were provided. The user is forced to replace the mouthpiece and airway with each replacement of the dose storage portion, so when the medicament within the storage portion has been exhausted a user is forced to replace the cartridge in order to continue to receive medicament doses. The cartridge includes an airway and a mouthpiece and it should be understood that one or both of the airway and mouthpiece may comprise a cover or sleeve, for example a flexible membrane, which fits onto or over a structure provided on the inhaler, for example on the body, so that the cartridge need not provide the structural elements of the airway and/or the mouthpiece, but provides the surface which defines the airway and mouthpiece in use. In one embodiment the airway and mouthpiece are substantially rigid.

The replacement cycle for the mouthpiece and airway is therefore determined by the number of doses stored within the storage portion and dosage frequency for said medication. In some embodiments the storage portion contains more than 5 doses, more than 7 doses or more than 13 doses. In some embodiments the storage portion contains less than 50 doses, less than 30 doses or less than 15 doses. In one embodiment the storage portion contains between 5 and 20 doses and in another between 6 and 15 doses. In some embodiments the user is intended to take the medication only once a day and in other embodiments the user is intended to take the medication at least twice a day. This therefore provides a limit on the number of doses that can be taken through the same mouthpiece and airway and the length of time during which a mouthpiece and airway are in use.

It should be understood that the term mouthpiece is used herein to mean a part of the device that enters, or makes contact with a user to enable them to make a suitable seal with the device to allow then to inhale from the device. In some embodiments the mouthpiece will be a part adapted to be placed in the mouth of a user, for example between the lips or between the teeth, so that a user can inhale from the device. In other embodiments the mouthpiece could be a part adapted to be placed on, in, or up, the nose of a user to enable then to inhale through the device.

The invention also provides an inhaler, the inhaler including a body and a cartridge, the cartridge comprising a dose storage portion and the cartridge being releasably coupled to the body, the dose storage portion being suitable for containing a plurality of doses of an inhalable medicament, the inhaler device configured and arranged such that a dose of inhalable medicament from the dose storage portion can be accessed and arranged in a delivery configuration for delivery to a user, the inhaler characterised in that the cartridge comprises at least one actuator extending therefrom which can be actuated by a user, the actuator and cartridge being arranged such that, when actuated, a dose of inhalable medicament from the dose storage portion can be accessed and arranged in a delivery configuration for delivery to a user.

By providing a cartridge that includes an actuator it is possible to reduce the mechanical complexity and needs for tightly controlled tolerances of the interface between the body and the cartridge. Providing an actuator on the cartridge allows a user to provide mechanical input directly into the cartridge to cause movement within the cartridge, for example dose movement, blister advance or a combination of the two actions, possibly with one or more other actions. This removes the need for significant mechanical transfer across the interface between the body and cartridge which allows for a reduced overall parts count for the inhaler and also allows a reduction of the number of moving parts within the body which might increase the mechanical reliability of the body allowing it to be used for longer.

The invention further provides an inhaler, the inhaler including a body and a cartridge, the cartridge comprising a dose storage portion and the cartridge being releasably coupled to the body, the dose storage portion being suitable for containing a plurality of doses of an inhalable medicament, the inhaler device configured and arranged such that a dose of inhalable medicament from the dose storage portion can be accessed and arranged in a delivery configuration for delivery to a user, the inhaler characterised in that when coupled together a coupling area of the cartridge arranged adjacent the body and is inaccessible to a user, the area of the coupling area being less than the contactable surface area of the cartridge which remains accessible when the body and cartridge are coupled together.

By designing the inhaler to have a body which does not substantially cover a majority of the cartridge surface the body can be made more compact. By having a majority of the cartridge surface accessible when the body is coupled to the inhaler the user is provided with easy access to grasp the cartridge when needed. The shape of the replaceable cartridge can be changed if desired to alter the ergonomics of the inhaler to suit particular patient populations, medicaments or for other reasons without the need for a change in the body design. The area of the coupling may be less than 75% of the contactable surface area of the cartridge, or may be less than 50%. The external surface area of the cartridge excluding the coupling area may include gripping surfaces located on opposed surfaces to facilitate gripping by a user.

It should be noted that, for these surface area comparisons, a simplified 'block' model of the cartridge, comprising simple geometric shapes, is assumed. The coupling area may have a very complex shape which could result in a high measured actual surface area, but the block model substantially simplifies the shape so that the outer surface of the cartridge comprises planar regions, or gentle curves, which renders the surface area of the external, user contactable surface, comparable with the coupling area.

It should be noted that the different features provided by the invention can be used individually in some embodiments, or one or more of the features could be used in combination with others.

The cartridge may be releasably secured to the inhaler body using any suitable mechanism. For example resiliently biased catches may be provided on one, or both, of the body and cartridge. These catches may engage with corresponding detents on the other, or both, of the body and cartridge. In one embodiment the catches and detents may cooperate to hold the cartridge to the body until a user applies a separation force to the body and cartridge to pull them apart. In another embodiment buttons or releases may be provided which must be actuated by the user to release the catches from the detents to enable easy separation of the body and cartridge. In other embodiments there may be provided releasable locks on one, or both, of the body and cartridge which must be released by a user before the body and cartridge can be separated. It is possible that one or more of these mechanisms can be combined. In one embodiment catches are provided that need not be released by a user before separation of the body and cartridge is possible. Such an arrangement can help prevent damage to the body and/or cartridge if the inhaler is dropped when the body and cartridge are coupled together as the parts tend to separate with a reduced risk of damaging the catches and/or detents. In some such embodiments a button or release may be provided to facilitate separation should a user wish to use such a mechanism.

The attaching of the cartridge to the body to form the inhaler enables delivery of a medicament from within the cartridge. The cartridge may not be able to deliver a medicament contained therein to a user during an inhalation action without being coupled to the body to form the inhaler, for example it may lack a complete mechanism to access and deliver a dose of medication. For example it may not include a complete piercing mechanism or a complete dose deagglomeration mechanism. In some embodiments the delivery of medicament from the cartridge may be prevented by, for example, a lockout mechanism which is only deactivated when the cartridge is coupled to the body, for example it may not be possible to open a cover attached to the cartridge until the cartridge is coupled to the body. Such a mechanism could be integrated into catches that hold the body and cartridge together so that when a catch is engaged, it deactivates a lockout mechanism thereby allowing actuation of the mechanisms within the cartridge, for example a dose moving mechanism. In another embodiment the cartridge may include a lockout which substantially prevents actuation of the cartridge when not attached to the body. In some embodiments the body comprises at least one controller for operating at least part of the cartridge. In one embodiment the body may comprise an electronic controller that actuates a piercing mechanism within the cartridge to pierce a blister within the cartridge so that the medicament therein can be delivered to a user when the user inhales through the inhaler. In the same or other embodiments the body may comprise a deagglomeration mechanism which, in use, supplies energy to a powdered medicament arranged in a delivery location within the cartridge to assist in the deagglomeration of the powder.

The cartridge may include a display area within which dose indicia are displayed indicative of the number of doses remaining in, or dispensed from, the cartridge. The body may include a window through which the display area of a cartridge attached to the body is visible. By providing such a window the perceived value of the body may be increased and a user is less likely to mistakenly discard the body instead of the cartridge. This may be particularly important for some embodiments in which the body is smaller than the cartridge.

The body may comprise a lanyard attachment point to further enhance the perceived value of the body.

In one embodiment the body includes an attachment side to which a corresponding side of a cartridge can be attached to couple the body to the cartridge. By coupling only a side of the body to the cartridge the body need not be comparable in size to the cartridge as the body does not need to contain the cartridge.

The body may include a foot at its base. The body may be able to stand up on the foot when not attached to a cartridge and the inhaler may be able to stand on the foot when the body is attached to the cartridge.

In one embodiment the body includes an attachment side and a foot which extends from the base of the attachment side. The foot may extend substantially perpendicular to the direction in which the attachment side extends.

In some embodiments the cartridge may be smaller in size than the body and fits into a recess in the body so that the cartridge is located substantially within the body with the mouthpiece projecting therefrom. In other embodiments the cartridge is larger than the body and the body is coupled to the cartridge, rather than the cartridge being received within the body. The cartridge may be at least 10% larger in volume than the body, or may be at least 20%, at least 50% or least 100% larger than the body.

In one embodiment the dose storage portion is adapted to contain a plurality of pre-metered doses of an inhalable medicament. In another embodiment the pre-metered doses of an inhalable medicament are contained in a plurality of containers, such as blisters, each container containing a dose of medicament. The dose storage portion may contain a reservoir of powder from which a dose can be metered within the inhaler during use.

The term a delivery configuration is used herein to refer to a configuration in which a dose of medication is removed from the storage portion and to a position in which the dose can be delivered to a user. This may be by metering a dose from a reservoir and moving the metered dose into an airflow channel from which it can be entrained in a user's inhalation airflow. In one embodiment the arrangement of a dose in the delivery configuration involves the movement of a dose containing blister from the storage portion to a position outside the storage portion in which the medicament from the blister can delivered to a user, for example the blister may be opened and the medicament therein released for inhalation by a user. All operations performed for delivery need not occur in this position, for example the blister may be opened, for example by piercing, as it is moved to a delivery position or when it is there.

The term dose is used herein to indicate a unit portion of a medicament. The unit portion may be all, or part, or an aliquot of a therapeutic, or suggested, dose which forms part of a treatment regimen. The term medicament is used herein to refer not only to a formulation including a therapeutically active component, but also to a placebo of such a formulation.

In one embodiment the cartridge further includes a cover which is movable between a protection position in which the cover substantially covers the mouthpiece and a use position in which the mouthpiece is exposed. The inclusion of a cover provides environmental protection for the mouthpiece when the device is not in use, for example it is being carried in a bag. By mounting the cover on the cartridge the movement of the cover between the two positions can be readily harnessed to provide work within the cartridge, for example using simple mechanical linkages, for example the cover could be coupled to the actuator, either directly or via a mechanical linkage, for arranging a dose in the delivery configuration. In some embodiments the cover provides the actuator on the cartridge described above. For example the movement of the cover could be used to arrange a dose in the dispensing configuration for delivery to a user, to open or unseal a dose container or to prime an energy storage mechanism, for example by compressing a spring, or other energy storage element, or a combination of these. The cartridge may also include an external drive from which the body, or other component connected to the cartridge can receive mechanical, or other, energy. Such a drive portion could be used to transfer some of the energy of moving the cover into the body to provide a source of mechanical, or other, energy within the body. For example the energy transferred to the body could be used to open or unseal a dose container or to prime an energy storage mechanism, for example by compressing a spring or other energy storage element.

Energy stored in the cartridge or body could be used to drive a mechanism, for example an opening mechanism, such as a piercing or peeling mechanism by which a medicament container is unsealed. The energy stored could also be used to assist deagglomeration of the powdered medicament before or during inhalation.

In one embodiment the body of the inhaler includes a deagglomeration mechanism to assist deagglomeration of the powdered medicament from dose container. It should be understood that the cartridge may also include a deagglomeration mechanism instead of, or in addition to, a deagglomeration mechanism in the body. The deagglomeration mechanism may comprise an energy source and a transducer, the transducer being arranged to receive energy from the energy source and transfer at least some of that energy to a dose of inhalable medicament to assist the deagglomeration of said inhalable medicament. It is also possible for such a deagglomeration mechanism to be split between the body and cartridge, for example with the cartridge comprising the energy source and the body comprising the transducer and there being an energy transfer coupling between the body and cartridge to allow the energy to pass to the transducer. In one embodiment the energy source is a source of electrical energy and the transducer includes a vibrating element. In one embodiment the vibrating element comprises a piezoelectric element. In some embodiments a majority of complex or expensive parts, or parts that are likely to wear, are included in the body which leaves the cartridge to comprise comparatively simple mechanisms, such as moulded parts.

In some embodiments it may be necessary or desirable to couple a moving part in the cartridge with a moving part in the body to transfer energy between the two parts. This can be achieved using a mechanical linkage which is linked when the cartridge is attached to the body. In another embodiment the body contains components that are sensitive to the environmental conditions, for example electronics which are sensitive to moisture. In such an embodiment several surfaces of the body may co-operate to substantially seal an interior volume to protect the sensitive components. Should a mechanical linkage be required between the cartridge and the sealed interior volume of the body it may be made through a flexible membrane which extends over, and substantially seals, an opening in a surface of the body. The surface of the body in which the opening is formed and which is sealed may form part of the attachment side.

The body may include a processor and memory. The processor can be used to receive signals from one or more sensors arranged in, or on, the body or a cartridge attached thereto, process the signals and then store data in the memory. The stored data may be representative of the breathing profile of the user, for example the body of cartridge may include one or more of a pressure sensor or a flow sensor, the time and date of the activation of the device, other physiological characteristics of the user for which the device includes a sensor, for example the user's body temperature, environmental characteristics such as air temperature and or humidity. The body may have different settings which could be manually or automatically selected depending upon the cartridge coupled to the body, for example different blisters may require a different piercing depth.

The body may be coupled to a training cartridge which may not contain any medicament. The training cartridge may include more sensors than are found in a normal medicament cartridge. The additional sensors may be used to monitor the way in which a user interacts with the device and provide signals to the processor in the body, or a processor in the cartridge. The processed signals may be stored on memory in the body or in the cartridge, or transmitted to an external device, for example a computer. The transmission may be via a wired connection, or a wireless connection, and may use any suitable communication protocol.

The invention also provides a method of preparing an inhaler kit for use, the inhaler kit comprising a body and a cartridge, the cartridge comprising a dose storage portion, the dose storage portion being suitable for containing a plurality of doses of an inhalable medicament, the method including the step of:

i) coupling the cartridge to the body to create an inhaler.

The method may include the additional step of:

ii) actuating the inhaler to cause a dose of inhalable medicament from the dose storage portion to be accessed and arranged in a delivery configuration for delivery to a user.

In one embodiment, the cartridge includes a cover movable between a first position in which the cover substantially covers the mouthpiece and a second position in which the mouthpiece is accessible for use and the method further comprises the step of moving the cover from the first position to the second position.

The invention further extends to a body suitable for use with the inhaler kit as described above and to a cartridge suitable for use in the inhaler kit described above.

It should be understood that throughout this specification and in the claims that follow, unless the context requires otherwise, the word "comprise", or variations such as "comprises" or "comprising", implies the inclusion of the stated integer or step, or group of integers or steps.

DRAWINGS

The invention will now be further described, by way of example only, with reference to the following drawings in which.

Figure 3:
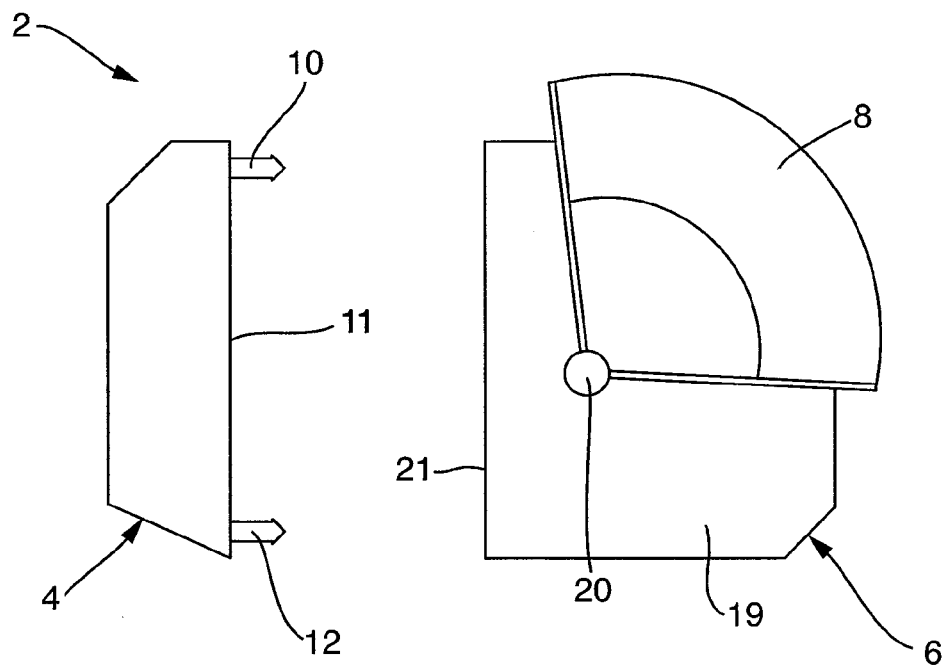
FIG. 3 shows the parts of a second embodiment of an inhaler kit comprising a body and a cartridge.
Figure 4:
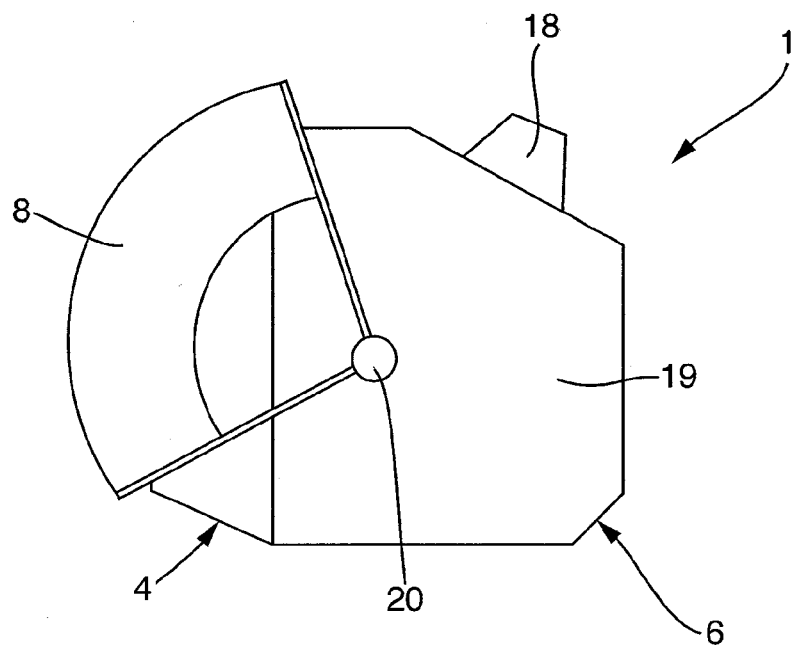
FIG. 4 shows an inhaler created from the kit of FIG. 3 in a dispensing configuration.
Figure 5:
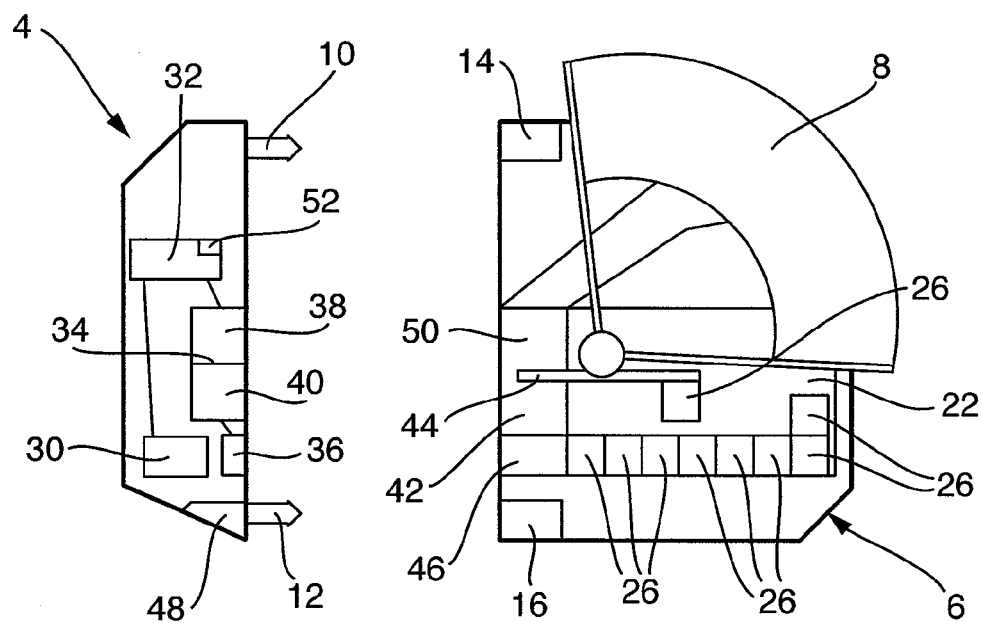
Figure 6:
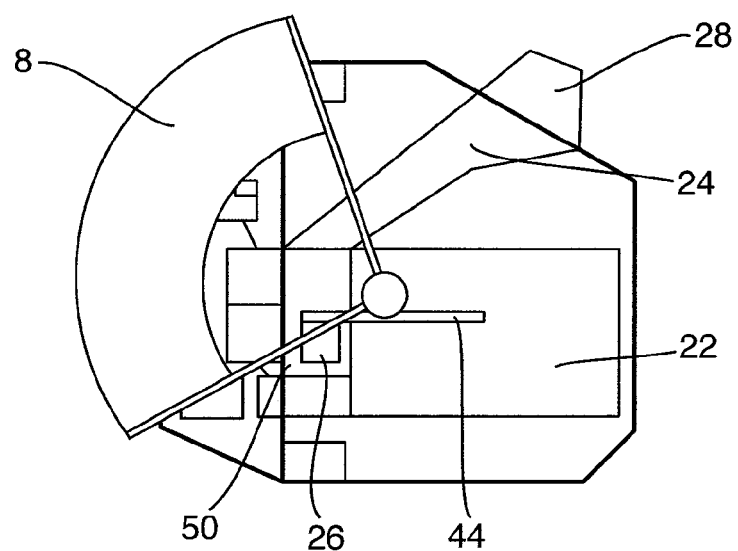
Figure 7:
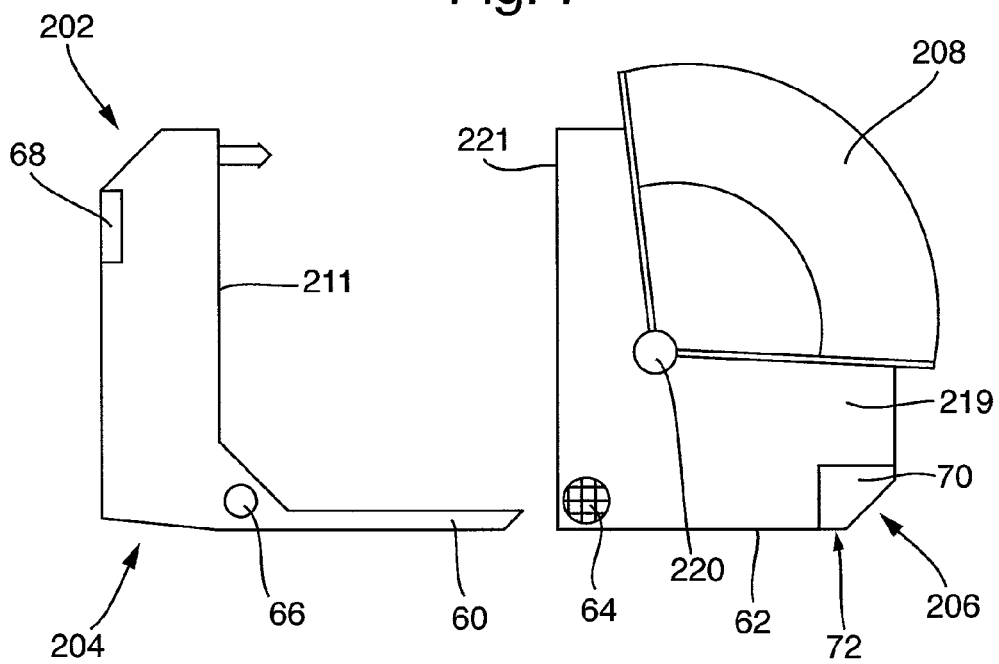
Figure 8:
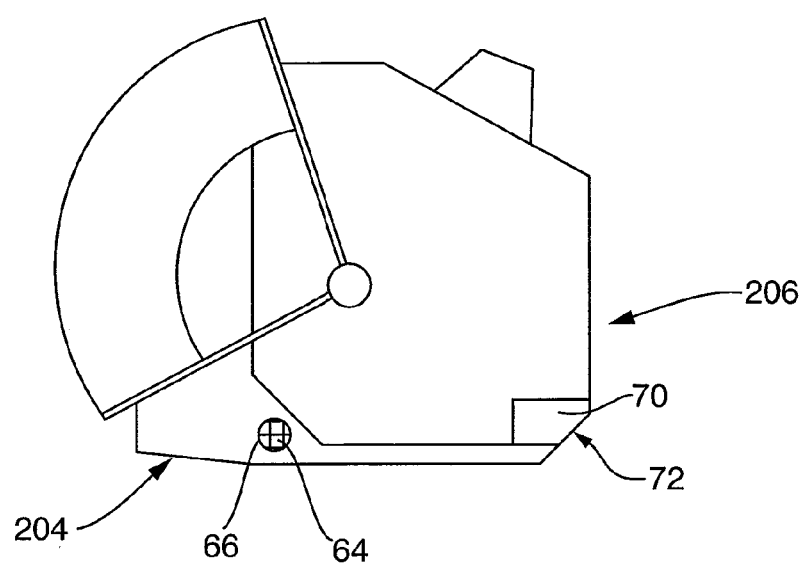

FIGS. 5 and 6 show schematic versions of FIGS. 3 and 4 showing internal parts; and FIGS. 7 and 8 show schematic versions of an inhaler similar to that in FIGS. 3 and 4 but including a foot.

DETAILED DESCRIPTION

Figure 1:
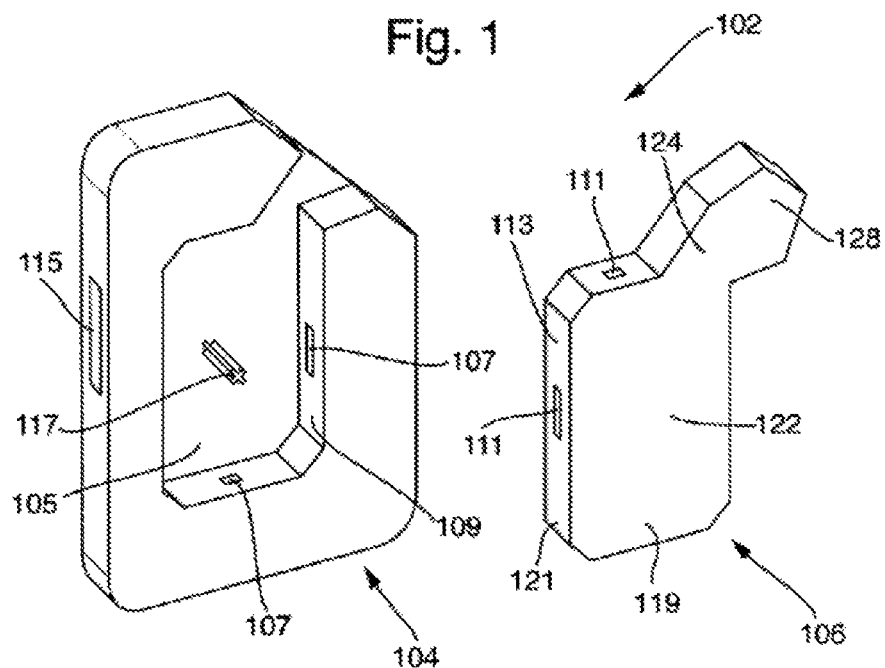
FIG. 1 shows the parts of an inhaler kit comprising a body and a cartridge.
Figure 2:
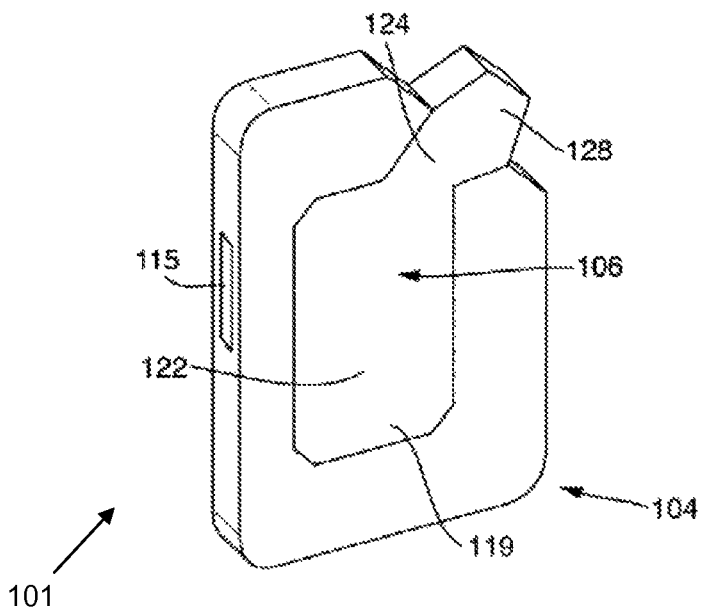
FIG. 2 shows an inhaler created from the kit of FIG. 1 in a dispensing configuration.

FIGS. 1 and 2 show a kit of parts 102 that can be assembled to create an inhaler 101. The inhaler 101 including a body 104 and a cartridge 106. The cartridge 106 comprises a dose storage portion 122 and an airway 124. The dose storage portion 122 is suitable for containing a plurality of doses of an inhalable medicament. The airway 124 includes a mouthpiece 128 at an end thereof. The inhaler device 1 is configured and arranged when assembled such that a dose of inhalable medicament from the dose storage portion 122 can be accessed and arranged in a delivery configuration for delivery to a user through the airway 124 upon inhalation through the mouthpiece 128 by a user. In this case the mouthpiece 128 is adapted top be placed between the lips of a user (not shown). The cartridge 106 is replaceably removable from the body 104. In this embodiment, the body includes a recess 105 into which the cartridge 106 can be fitted. The recess 105 includes projecting ridges 107 on an inner surface 109 thereof which engage with corresponding recesses 111 on an outer surface 113 of the cartridge 106 to releasably retain the cartridge 106 in the body 104.

The body 104 includes a button 115 that a user can actuate to drive a spindle 117 which, when the body 104 and cartridge 106 are coupled together, is engaged in the cartridge 106 and causes a dose of medicament to be arranged as required.

In this embodiment of an inhaler 1, the cartridge is received into a recess 105 in the body 104 so, when coupled together the contactable surface area 119 of the cartridge 106 which remains accessible is smaller than the coupling area 121 which is the area of the cartridge 106 rendered inaccessible to a user when the cartridge 106 is coupled to the body 104.

FIG. 3 shows a kit of parts 2 to create an inhaler 1. The kit 2 comprises a body 4 and a cartridge 6. The cartridge 6 including a cover 8 which is movable between a first position (as shown in FIG. 3) and a second position (as shown in FIG. 4).

The body 4 includes projecting catches 10,12 on an attachment side 11 which, when inserted into corresponding catch receiving portions 14,16 (shown in FIGS. 5 and 6) of the cartridge 6, couple the body 4 and cartridge 6 together to create an inhaler 1. At least one of the catch receiving 14,16 portions deactivates an interlock when a catch 10,12 is inserted therein, the deactivation of the interlock allowing at least one mechanism within the cartridge to be actuated.

FIG. 4 shows an inhaler 1 created from the kit 2 of FIG. 3. As shown in FIG. 4, the cover 8 has been moved into the second position in which a mouthpiece 18 is exposed so that it can be used. In the first position, as shown in FIG. 3, the cover 8 substantially restricts access to the mouthpiece 18.

To move the cover 8 from the first position to the second position the cover is pivoted about a pivot point 20. In this embodiment the mouthpiece cover 8 is coupled to the cartridge 6 and acts as an actuator that can be actuated by a user to operate parts of the cartridge as described in more detail below.

In this embodiment the attachment at a side 11 of the body and cartridge 6 allows the contactable surface area 19 of the cartridge 6 which remains accessible to be larger than the coupling area 21 which is the area of the cartridge 6 rendered inaccessible to a user when the cartridge 6 is coupled to the body 4.

FIGS. 5 and 6 show schematic versions of FIGS. 3 and 4 showing internal parts and mechanisms. It should be understood that these figures are simply schematic diagrams and do not necessarily show the actual layout or shape of particular features. The schematic diagrams do however illustrate that for this inhaler, when coupled together, a coupling area of the cartridge arranged adjacent the body and is inaccessible to a user, the area of the coupling area is less than the contactable surface area of the cartridge which remains accessible when the body and cartridge are coupled together.

FIG. 5 shows a kit of parts 2 to create an inhaler 1 and FIG. 6 shows an inhaler made from the kit 2. The kit 2 comprises a body 4 and a cartridge 6. The cartridge 6 comprising a dose storage portion 22 and an airway 24. The dose storage portion 22 contains plurality of dose containers 26, in this case blisters, each of which contain a dose of an inhalable medicament. The airway 24 includes a mouthpiece 28 at an end thereof and the inhaler device is configured and arranged such that a dose 26 of inhalable medicament from the dose storage portion 22 can be accessed and arranged in a delivery configuration for delivery to a user through the airway 24 upon inhalation through the mouthpiece 28 by a user. FIG. 5 shows a plurality of dose containers 26 stored in the dose storage portion 22 of the cartridge 6.

The body 4 includes a power source 30, in this case a battery, which is connected to a control unit 32, in this case an electronic processing unit, which is connected to a transducer portion 34. In this case the transducer portion 34 includes a deagglomeration assisting unit 38, in this case an electrically driven vibrating piezoelectric element to assist deagglomeration of the dose 26 of medicament. The control unit 32 in this embodiment is also connected to a sensor 52 which is able to detect when a user is inhaling through the mouthpiece 28.

As shown in FIG. 5, the body 4 further includes a drive receiving unit 36 which can receive a mechanical, or other, drive from the cartridge 6. The drive receiving unit 36 is coupled to the transducer unit 34 and supplies received energy thereto. It should be understood that although a single transducer portion is shown which contains two different transducers, there may be more than one transducer portion 34 within the body 4 and each may contain one or more transducers which receive energy from one or both of the energy source 30 or the drive receiving unit 36. The transducer portion 34, in addition to, or instead of, the deagglomeration assisting unit 38 may include a dose access unit 40, for example a peeling, piercing or tearing mechanism which is operable to open a dose container 26 which has been moved from the dose storage portion 22 to a dose opening location 42 so that the medicament therein can be dispensed from the inhaler 2.

As shown in FIG. 5 the cartridge also includes a drive mechanism 44 which is coupled to the cover 8 such that the drive mechanism 44 is driven by movement of the cover 8 between the first and second positions. In this case the drive mechanism 44 is operable to move a dose container 26 of medicament from the dose storage portion 22 to the opening location 42 as the cover 8 is moved from the first position to the second position. The drive mechanism 44 is further operable to move the dose container 26 of medicament back into the dose storage portion 22 as the cover 8 is moved from the second position to the first position. If the dose container 26 returned to the dose storage portion 22 has been opened, the drive mechanism 44 indexes to retrieve a different dose container 26 the next time the cover 8 is moved.

The cartridge also includes an external drive 46 which is coupled to the cover 8 such that movement of the cover between the first and second positions drives the external drive 46. The external drive 46 is arranged such that when the body 4 is coupled to the cartridge 6 the external drive 46 can drive the drive receiving unit 36.

The airway 24 includes a mouthpiece 28 at an end thereof, as shown in FIG. 6. The mouthpiece 28 is protected by the cover 8 when the cover 8 is in the first position (as shown in FIG. 5) and is exposed for use when the cover 8 is in the second position (as shown in FIG. 6).

FIG. 6 shows the dose container 26 in the opening location 42 in which it can be opened by the opening unit 40. In this embodiment the opening location 42 is substantially the same as the dispensing location 50 in which the deagglomeration unit 38 can assist in deagglomeration of the dose of medicament during inhalation. It should be understood that the opening location 42 may not be the same as the dispensing location 50, for example a container containing the dose 26 of medicament may be opened as it is moved through the opening location 42 to the dispensing location 50.

To prepare the inhaler 1 for use from the kit 2 the body 4 and the cartridge 6 are coupled together using the projecting catches 10,12 which engage with the clip receiving portions 14,16 which include detents to retain the catches. The body 4 further includes a catch release button 48 which a user can press to facilitate release of the catch 12 from the catch receiving portion 16.

Once the body 4 and cartridge are coupled together a user can move the cover 8 from the first position to the second position. In the second position the mouthpiece 28 is exposed for use and, in this embodiment, the cover 28 extends over at least a portion of the body 4 which helps to prevent separation of the body 4 and cartridge 6 when the inhaler 1 is ready for use.

As the cover 8 is moved from the first position to the second position by rotation about the pivot 20 the drive mechanism 44 is driven to move a dose container 26 into the opening position 42. The external drive unit 46 is also driven by the movement of the cover 8 and transfers drive to the drive receiving unit 36 of the body 4 to prime the opening unit 40, in this case by tensioning a spring. The inhaler is now ready for a user to inhale through the mouthpiece and receive their dose of medicament.

As the user inhales through the mouthpiece 28 the control unit 32 receives a signal from the sensor 52 indicative of an inhalation event. The control unit 32 actuates the opening unit 40 to open the dose container 26 in the opening location 42 using the stored energy received from the drive receiving unit. The control unit 32 then activates the deagglomeration unit 38 which assists deagglomeration of the powder within, or leaving the dose container in the dispensing location 50 (in this case the same as the opening location 42) and being entrained in the inhalation breath of the user.

After the user has received their dose of medicament the cover 8 is returned to the first position covering the mouthpiece 28. As the cover 28 is returned to the first position the drive mechanism returns the used dose container 26 to the dose storage portion 22 and indexes to the next dose container 26 stored therein. If no inhalation event occurred then the dose container 26 returned to the dose storage portion 22 will still be unopened and the drive mechanism will not index to the next dose container 26.

With the cover 28 in the first position the body 4 and cartridge 6 can be separated and a different cartridge coupled to the body 4. This allows the body 4 of the inhaler kit 2 to be retained and the cartridge to be replaced.

FIGS. 7 and 8 show schematic images of an inhaler 202 similar to that in FIGS. 3 and 4 but including a foot 60. The schematic diagrams illustrate that for this inhaler, when coupled together, the coupling area of the cartridge which is arranged adjacent the body and is inaccessible to a user is larger than it was for the inhaler of FIGS. 5 and 6, but is still less than the contactable surface area of the cartridge which remains accessible when the body and cartridge are coupled together.

The foot 60 extends substantially perpendicular to the attachment side 211. The foot 60 extends away from the attachment edge 211 such that a lower side 62 of the cartridge 206 substantially fits onto the foot 60 when the cartridge 206 is attached to the body 204 as shown in FIG. 8. In this embodiment the contactable surface area 219 of the cartridge 206 which remains accessible to be larger than the coupling area 221 which is the area of the cartridge 206 rendered inaccessible to a user when the cartridge 206 is coupled to the body 204.

The cartridge 206 also includes a display area 64 within which dose indicia are displayed indicative of the number of doses remaining in, or dispensed from, the cartridge 206. The body 204 includes a window 66 through which the display area 64 of a cartridge 206 attached to the body 204 is visible as shown in FIG. 8. The body 202 also include a lanyard attachment point 68.

In this example grip surfaces 70,72 is also provided on the cartridge 206 on opposing sides of the cartridge 206. The grip surfaces 70,72 may be shaped, textured or otherwise adapted to facilitate grasping by a user to facilitate separation of the body 204 and cartridge 206.

It should be understood that the invention has been described above by way of example only and that modifications in detail can be made without departing from the scope of the claims.

The invention claimed is:

1. An inhaler, the inhaler including a body and a cartridge, the cartridge comprising a dose storage portion and an airway, the dose storage portion comprising a plurality of blisters, each blister containing a pre-metered dose of an inhalable medicament, an actuator mechanism mechanically engaged with the dose storage portion for accessing and arranging in a delivery configuration a dose of medicament, and the airway for conveying the dose of medicament to a user, the airway including a mouthpiece at an end thereof, the inhaler device configured and arranged such that each of the plurality of blisters from the dose storage portion can be accessed and arranged in a delivery configuration for delivery to a user through the airway upon inhalation through the mouthpiece by the user, the cartridge being replaceably couplable to the body and characterised in that when the cartridge is coupled to the body a coupling area of the cartridge is arranged adjacent to the body and is inaccessible to a user, the area of the coupling contact area being less than the contactable surface area of the cartridge which remains accessible when the body and cartridge are coupled together, and wherein the body comprises a deagglomeration mechanism, and an electronic controller that actuates a piercing mechanism within the cartridge to pierce each of the plurality of blisters.

2. An inhaler as claimed in claim 1, in which the cartridge further includes a cover, the cover being movable between a protection position in which the cover substantially covers the mouthpiece and a use position in which the mouthpiece is exposed.

3. An inhaler as claimed in claim 1 wherein, the deagglomeration mechanism comprises an energy source and a transducer, the transducer being arranged to receive energy from the energy source and transfer at least some of that energy to the blister containing said pre-metered dose of inhalable medicament.

4. An inhaler as claimed in claim 3, in which the energy source is a source of electrical energy and the transducer includes a vibrating element.

5. An inhaler as claimed in claim 4, in which the vibrating element comprises a piezoelectric element.

6. An inhaler as claimed in claim 1, in which the cartridge includes a dose display area and the body includes a window through which at least a portion of the display area is visible when the cartridge is attached to the body.

7. An inhaler as claimed in claim 1, in which a cover is coupled to the actuator such that movement of the cover actuates the actuator, the cover being movable between a protection position in which the cover substantially covers the mouthpiece and a use position in which the mouthpiece is exposed.

8. An inhaler as claimed in claim 1, in which arranging the blister in the delivery configuration comprises movement of the blister from the storage portion to a position outside the storage portion.

9. An inhaler as claimed in claim 1, in which the cartridge also includes a drive mechanism which is coupled to an actuator such that the drive mechanism is driven by movement of the actuator between first and second positions, the drive mechanism being operable to move a blister from the dose storage portion to an opening location as the actuator is moved from the first position to the second position, the drive mechanism being further operable to move the blister back into the dose storage portion as the actuator is moved from the second position to the first position, the drive mechanism further comprising indexing to retrieve a different blister the next time the actuator is moved if the blister has been opened.

* * * * *